United States Patent [19]

Kraus et al.

[11] 4,159,728
[45] Jul. 3, 1979

[54] HOT WATER BAG

[75] Inventors: Friedrich Kraus, Stuttgart; Berthold Kalbas, Krumbach, both of Fed. Rep. of Germany

[73] Assignee: Gummi-Kraus GmbH, Stuttgart, Fed. Rep. of Germany

[21] Appl. No.: 880,891

[22] Filed: Feb. 23, 1978

[30] Foreign Application Priority Data

Mar. 12, 1977 [DE] Fed. Rep. of Germany ... 7707739[U]

[51] Int. Cl.² ............................................. A61F 7/04
[52] U.S. Cl. ................................. 150/2.1; 128/403; 150/8
[58] Field of Search ............... 150/2.1, 2.2, 2.3, 2.4, 150/2.5, 2.6, 2.7, 8, 52 E; 128/258, 403

[56] References Cited

U.S. PATENT DOCUMENTS

| 1,857,087 | 5/1932 | Lindemann | 150/2.1 |
| 2,043,327 | 6/1936 | Miller | 150/52 E |
| 2,136,043 | 11/1938 | De Laney | 150/2.1 |
| 3,610,307 | 10/1971 | Huff | 150/2.1 |
| 3,906,129 | 9/1975 | Damois | 150/2.2 X |

FOREIGN PATENT DOCUMENTS

| 361977 | 11/1931 | United Kingdom | 150/2.1 |
| 1383536 | 2/1975 | United Kingdom | 128/403 |
| 1455672 | 11/1976 | United Kingdom | 150/8 |

*Primary Examiner*—Donald F. Norton
*Attorney, Agent, or Firm*—Michael J. Striker

[57] ABSTRACT

A hot water bag made of a soft, flexible, rubber-like synthetic material and defining two side walls of a substantially rectangular shape and having a filling neck at a shorter side thereof, comprising a soft flexible coat seam-welded to at least one of said side walls. The hot water bag is manufactured by injection die molding process in assembled outer molds including a core; the bag body with embedded filling neck is first manufactured with a side slit for removing the die core then the pliant coat is seam welded to one side and finally the slit between the side walls is closed by welding.

7 Claims, 5 Drawing Figures

HOT WATER BAG

BACKGROUND OF THE INVENTION

The present invention relates to a hot water bag of a soft flexible material having a flat, in a plan view substantially rectangular configuration, and a filling neck projecting from a shorter side thereof. Conventionally hot water bags of this type are made of rubber. They may be provided on the upper surface thereof with ribs so that excessively hot water does not cause burning when the bag is in contact with the skin. To improve heat insulation it is known to enclose the rubber walls into a cloth covering. This measure however results in substantially increased manufacturing costs and in use it brings about an additional cleaning work.

It is an object of this invention to provide a hot water bag having an upper surface that is pleasant for contact with the skin.

Another object of this invention is to improve heat insulation of the bag.

Further object of this invention is to provide a hot water bag which can be manufactured at a low cost.

Still further object of this invention is to provide a hot water bag which can be easily cleaned.

SUMMARY OF THE INVENTION

In accordance with the above objects, and others which will become apparent hereafter, one feature of this invention resides in the provision of a hot water bag which includes in combination, a heat radiating body made of a rubber like synthetic material and a pliant coat provided at least on one of its side walls.

The use of a commercially inexpensive synthetic material makes it also possible to connect immediately to the upper surface of the bag a coat which has a certain heat insulating effect, produces soft and pliable sensation and moreover permits many variations of optically attractive embodiments thereof. With advantage the coat is welded to the side wall of the bag along its periphery, and follows substantially the edge of the wall. In a particularly advantageous modification, the coat consists of a plastic foil, connected with a layer of foam material; for technological reasons as well as for good appearance and a good cushioning effect, the plastic foil may be connected to the foam material by seam welding which on the viewing side may produce recesses or bas-relief having ornamental effect. In welding the open edge of the bag, the peripheral portion of the coat is recessed into the side wall of the bag so that an additional protection against an unintentional separation is achieved.

In the case that one side wall is free of coating, so it is advantageous to corrugate its upper surface by creating raised portions from the base surface, such as ribs or fins or an impressed pattern so that one or the other side might be selectively brought into contact with human body, depending on temperature sensitivity of the user or on the sensation resulting from contact with the upper surface.

According to another feature of this invention, the material for the hot water bag is of a thermoplastic or an elastomeric synthetic material, especially of a soft PVC. The filling neck contains a socket for receiving a closing plug; to insure secure connection between the socket and the bag body, the socket is provided with projections, such as two ring-shaped flanges for example. The flanges may have notches or openings which in the manufacture are filled up with the synthetic material. The socket is preferably made of a thermoplastic synthetic material and may be either solid or hollow.

According to still another feature of this invention, the hot water bag is manufactured by injecting the synthetic material into a mold consisting of a core and of an outer die. The socket to be embedded into the synthetic material during the injection or extrusion process is inserted into the outer part of the injection die mold. To remove the core and to facilitate the application of the coating or coat, a slit is initially left open in the molded semi product. The pliant coat is welded to the side wall and subsequently the slit is closed, preferably by high frequency welding. The parts of the side walls of the semi product, between which the slit initially is left, may be provided in the area of the slit with marginal projections that in subsequent steps are connected by welding.

The novel features which are considered as characteristic for the invention are set forth in particular in the appended claims. The invention itself, however, both as to its construction and its method of operation, together with additional objects and advantages thereof, will be best understood from the following description of specific embodiments when read in connection with the accompanying drawings.

DESCRIPTION OF THE PREFERRED EMBODIMENTS

Figure 1:
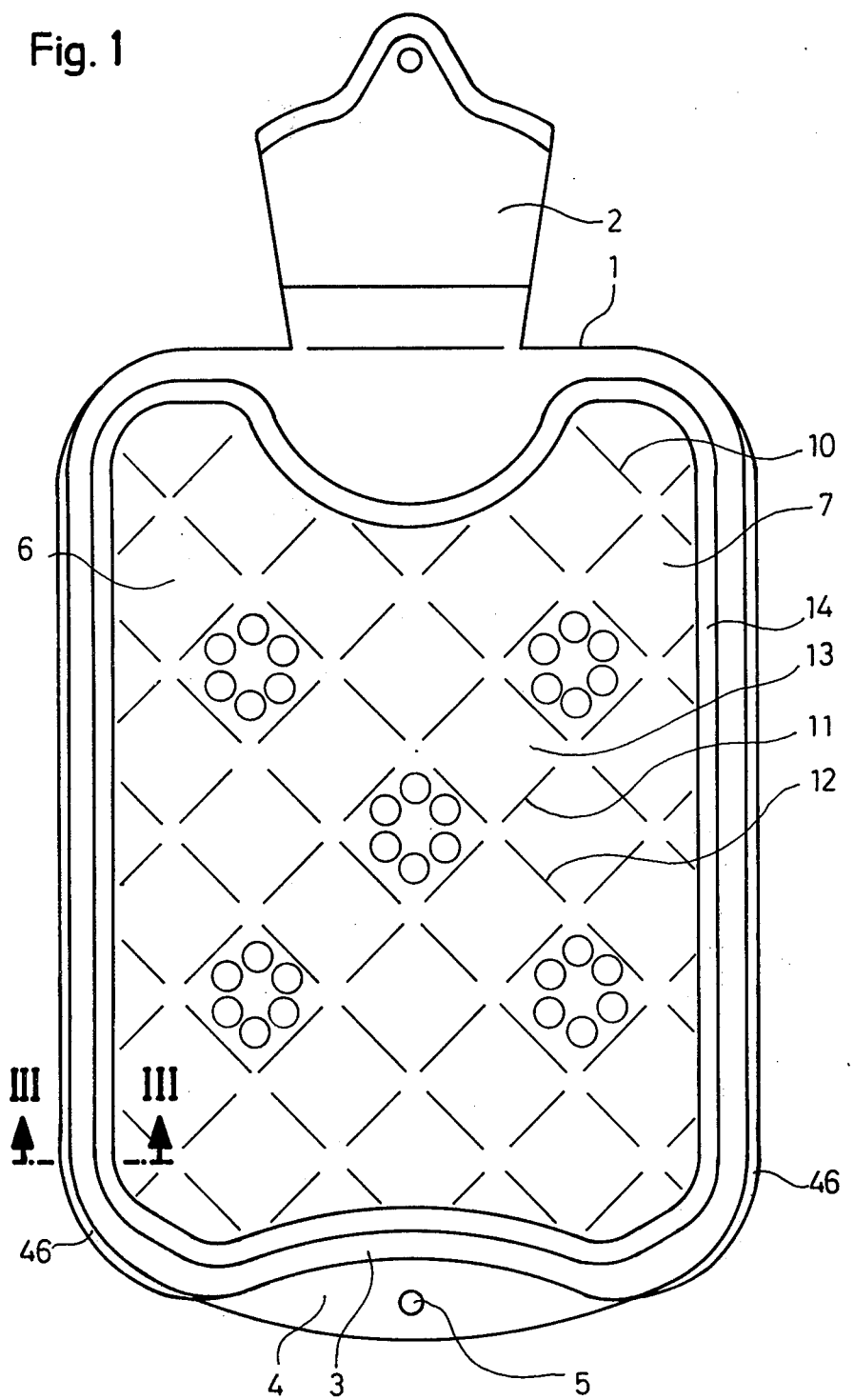
FIG. 1 is a plan view of one side of the hot water bag of this invention.
Figure 3:
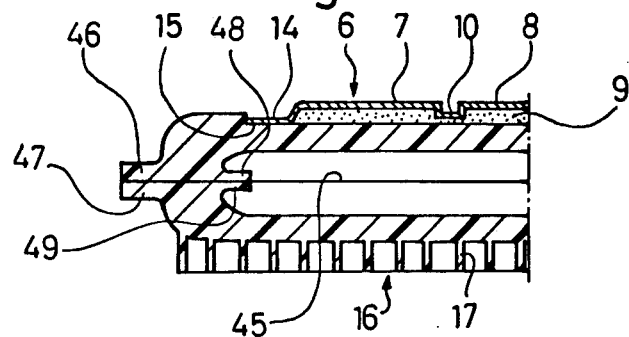
FIG. 3 is an enlarged sectional view of details taken along line III—III in FIG. 1.

Referring now to the drawing, the hot water bag of this invention has a flat, approximately rectangular configuration and is provided on one of its narrow sides (here 1) with a filling neck 2; the other narrow side 3 thereof may be provided with a lug or tongue 4 having a suspension eye 5. According to this invention, the upper side wall 6 is provided with a coat 7 consisting of a plastic foil 8 with foam layer or lining 9 (FIG. 3). The plastic foil 8 and the foam lining 9 are mutually connected along parallel, diagonal lines 11, 12, by weld stitches 10. The stitch welded lines 11 and 12 produce a pattern of quadratic fields 13 as can be seen particularly from FIG. 1. The plastic foil 8 may be embedded with an arbitrary ornamental pattern and made in any color. The plastic foil 8 is welded along its border 15 to the upper surface of the side wall 6. During the welding process, there results a continuous recess 15 which produces additional resistance against an unintentional separation of the foil 8 from the side wall 6. The edge or border 14 of the foil extends substantially parallel to the outline of the side walls of the hot water bag. At the narrow sides 1 and 3, the coat 6 is retracted inwardly so that its welding to the body of the side wall is not impeded by the filling neck. On the other narrow side the retraction provides room for the lug or tongue 4 with suspension eye 5.

On the opposite lower side wall 16 there is a plurality of narrow, parallel ribs 17 extending diagonally over the entire area of the side wall 16. By means of these ribs 17, the temperature of the upper surface of the lower side wall is reduced.

Figure 2:
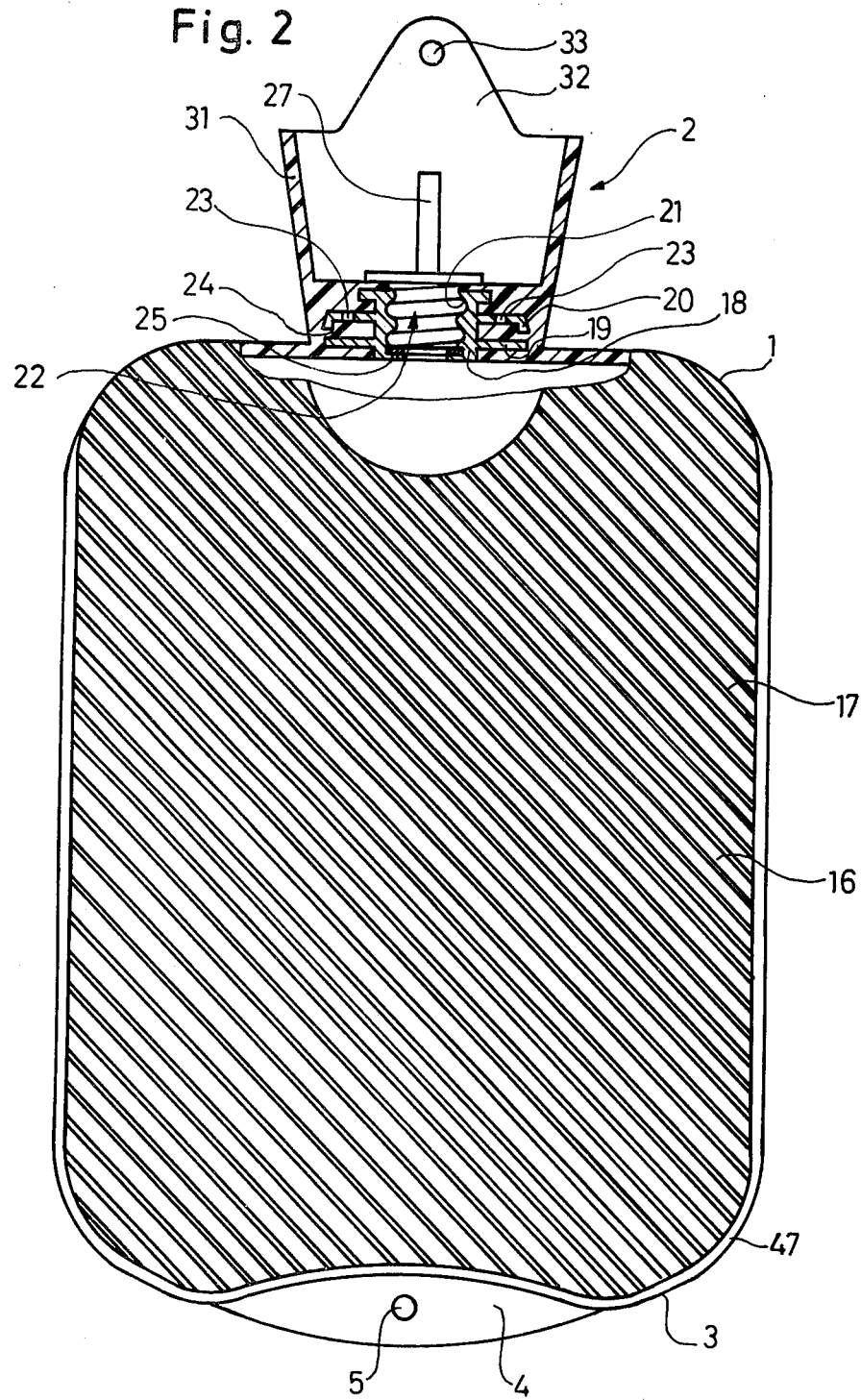
FIG. 2 is a plan view of another side of the hot water bag of FIG. 1 whereby the filling neck is shown in cross-section.

In the filling neck 2, there is embedded a socket 18 which on the outer side thereof has projections in the form of ring shaped flanges 19 and 20; in the embodiment shown in FIG. 2, the inside wall of the socket has screw threads 21 for engagement with windings of a closing plug 22. The flanges 19 and 20 cause a considerable increase of the upper surface of the socket so that the socket 18 is firmly anchored in the synthetic material of the bag body and insures a complete compactness and water tightness. The flange 20 can have openings or recesses for anchoring, such bore holes 23 which during the injection die molding process are filled with plastic or synthetic plastic, thus forming bridges passing therethrough. These bridges secure the plug 18 against rotation and also increase the compactness of the bag since the synthetic material forming the bag body is injected from both sides of the flange 20. An additional reinforcement of the embedding of the socket 18 in the filling neck area of the bag can be made by a circumferential undercut 24 on the flange 20.

If less than two flanges 19 and 20 be employed, the outer surface of the socket 18 would have to be provided with an adhesive agent, preferably with an adhesive that by virtue of its lattice like polymerization would harden to a temperature- and water-resistant connection or joint. Sealing ring 25 may be inserted into the socket 18 for abutment against the front surface of the closing plug 22.

Figure 4:
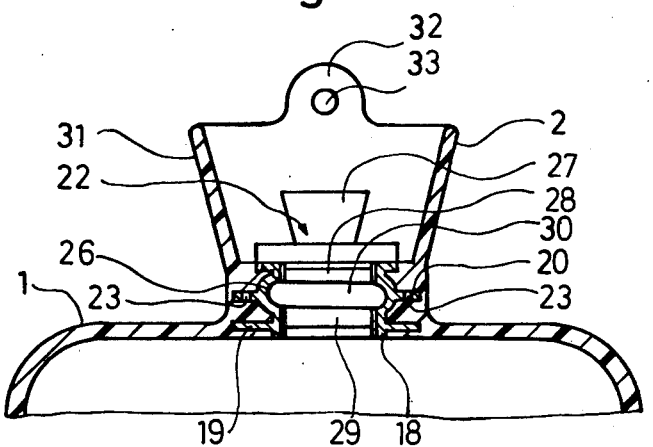
FIG. 4 is a sectional view of a part of the hot water bag showing a modification of its filling neck.

In another modification as shown in FIG. 4, the socket 18, instead of an inner screw thread 21, can be provided with a bulge 26 joining the flange 20 with its anchoring opening 23. In this case, the closing plug 22 has a lifting handle or strip 27 and a rubber ring 30 interposed between two abutment members 28 and 29. In turning the lifting handle 27, the abutments 28 and 29 are forced against each other by a screw member (not shown in the drawing) so that the rubber ring 30 becomes deformed outwardly and engages the interior of the bulge 26 in the socket 18 so that secure anchoring in axial direction is guaranteed and at the same time reliable sealing results.

To facilitate filling of the bag with hot water, the filling neck 2 has the shape of a funnel 31 that may be provided with a protruding lug or tongue 32 again with a suspension eyelet 33.

Figure 5:
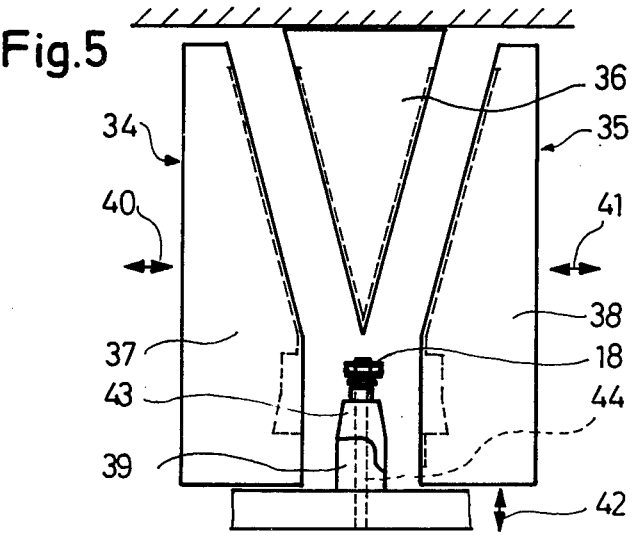
FIG. 5 is a schematic representation of an injection die mold for the manufacture of the hot water bag of this invention.

The hot water bag of this invention is manufactured of a rubber-like synthetic material, preferably of a soft PVC material by an injection die molding process. FIG. 5 shows schematically an example of an injection die mold 44. The mold consists of an outer die 35 and of a wedge like core 36. The outer die 35 itself is assembled of two mold parts 37 and 38 and of a front mold part 39. The mold parts 37 and 38 are displaceable in the direction of arrows 40 and 41 towards or away from the core 36 and the front mold part 39 is movable perpendicularly thereto in the direction of arrow 42. The mold parts 37 and 38 together with core 36 are designated for the manufacturing of side walls 6 and 16 of the bag and in connection with the front mold part 39 they also produce the filling neck 2. The front mold part 39 has a wedge shaped portion 43 corresponding to the interior of the funnel 31. The socket 18 may be held in position on the projecting end of the wedge-like member 43 by means of a rod 44, for example. Upon assembly of the mold, the injection of the synthetic material can be completed and upon a certain setting or hardening time the form is again disassembled and the semi-product bag including the embedded socket 18 is removed. In the resulting semi-product the filling neck 2 and the adjoining upper narrow side of the side walls form an enclosing part whereas the rest or both side walls hang down in a tongue-like fashion since upon the completion of the injection molding process, the two side walls are partially separated by a slit 45. Subsequently the marginal portion 40 of the coat 7 is welded to the upper side wall 6 whereupon the slit 45 is closed by a high frequency welding process. In the marginal area along the slit 45 the upper side wall 6 and the lower side wall 16 have, respectively, a projecting flange or rim 46 and 47 which facilitates the welding. In the welding process, inwardly projecting beads 48 and 49 are created as shown in FIG. 3. The peripheral rims 46 and 47 may be cut off during welding so that a neat outer shape might result.

While the invention has been illustrated and described as embodied in a preferred example of hot water bags, it is not intended to be limited to the details shown, since various modifications and structural changes may be made without departing in any way from the spirit of the present invention.

What is claimed as new and desired to be protected by Letters Patent is set forth in the appended claims:

1. A hot water bag having a substantially rectangular configuration and a filling neck at a narrow side thereof, comprising in combination two heat radiating side walls made of a soft, rubber-like synthetic material, a pliant coat provided on at least one of said side walls and including a plastic foil and an underlining of foam material connected to said foil, the periphery of said foil being secured to said side wall by welding.

2. A hot water bag as defined in claim 1, wherein the pliant coat follows substantially the edge of the adjacent side wall.

3. A hot water bag as defined in claim 2, wherein intermediate parts of opposite narrow edges of said coat are retracted inwardly.

4. A hot water bag as claimed in claim 1, wherein the other side wall opposite the side wall carrying said coating is provided on its upper surface with a plurality of ribs.

5. A hot water bag having a substantially rectangular configuration and a filling neck at a narrow side thereof, comprising in combination two heat radiating side walls made of a soft, rubber-like synthetic material, and a pliant coat secured at its periphery to at least one side of said walls, said pliant coat following substantially the edge of the adjacent side wall and the marginal portion of said coat being secured to said side wall by welding, and the welded marginal portion of said coat being seated in a recess formed in the adjacent side wall.

6. A hot water bag having a substantially rectangular configuration and a filling neck at a narrow side thereof, comprising in combination two heat radiating side walls made of a soft, rubber-like synthetic material, and a pliant coat secured at its periphery to at least one of said side walls, said pliant coat including a plastic foil connected to an underlining of foam material, said plastic foil and said foam lining being connected together by welding stitches.

7. A hot water bag as claimed in claim 6, wherein said stitch welds are arranged in an ornamental pattern.

* * * * *